(12) United States Patent
Bennett et al.

(10) Patent No.: US 12,156,688 B2
(45) Date of Patent: Dec. 3, 2024

(54) MICROBLADE STRUCTURE AND METHOD OF TREATING TISSUE

(71) Applicant: Solta Medical Ireland Limited, Dublin (IE)

(72) Inventors: Frederick Jay Bennett, Bellevue, WA (US); Craig Robert Bockenstedt, Bothell, WA (US); Gregory T. Wing, Carnation, WA (US)

(73) Assignee: Solta Medical Ireland Limited, Dublin (IE)

( * ) Notice: Subject to any disclaimer, the term of this patent is extended or adjusted under 35 U.S.C. 154(b) by 621 days.

(21) Appl. No.: 17/299,611

(22) PCT Filed: Dec. 5, 2019

(86) PCT No.: PCT/EP2019/083850
§ 371 (c)(1),
(2) Date: Jun. 3, 2021

(87) PCT Pub. No.: WO2020/115224
PCT Pub. Date: Jun. 11, 2020

(65) Prior Publication Data
US 2022/0015818 A1 Jan. 20, 2022

Related U.S. Application Data (60) Provisional application No. 62/776,120, filed on Dec. 6, 2018.

(51) Int. Cl.
*A61B 18/12* (2006.01)
*A61B 17/00* (2006.01)
(Continued)

(52) U.S. Cl.
CPC .... *A61B 18/12* (2013.01); *A61B 2017/00526* (2013.01); *A61B 2018/00083* (2013.01);
(Continued)

(58) Field of Classification Search
CPC .......... A61B 18/12; A61B 2017/00526; A61B 2018/00083; A61B 2018/00107; A61B 2018/0016; A61B 2018/1492
See application file for complete search history.

(56) References Cited

U.S. PATENT DOCUMENTS 6,050,988 A 4/2000 Zuck
8,781,576 B2 7/2014 Savage et al.
(Continued)

FOREIGN PATENT DOCUMENTS

CN 1281377 A 1/2001
CN 103263727 A 8/2013
(Continued)

OTHER PUBLICATIONS

Japanese Property Office, Notice of Reasons for Rejection issued in Patent Application Serial No. 2021-531993 on Sep. 8, 2023; 7 pages.
(Continued)

*Primary Examiner* — Linda C Dvorak
*Assistant Examiner* — Abigail Bock
(74) *Attorney, Agent, or Firm* — Thompson Hine LLP (57) ABSTRACT

Structures for treating tissue with high-frequency energy, methods of making a structure for treating tissue with high-frequency energy, and methods of treating tissue with high-frequency energy. A structure for use in treating tissue may include multiple microblades composed of an electrical conductor. Each of the microblades may include a shaft and a tip arranged adjacent to an end of the shaft. The tip includes multiple surfaces that surround a solid core of the tip and at least two of the surfaces may taper toward the end of the shaft.

20 Claims, 7 Drawing Sheets

(51) Int. Cl.
 *A61B 18/00* (2006.01)
 *A61B 18/14* (2006.01)
(52) U.S. Cl.
 CPC .............. *A61B 2018/00107* (2013.01); *A61B 2018/0016* (2013.01); *A61B 2018/1412* (2013.01)

(56) References Cited

U.S. PATENT DOCUMENTS

| | | | |
|---|---|---|---|
| 9,877,778 | B2 | 1/2018 | Manstein |
| 2002/0077584 | A1* | 6/2002 | Lin .................. A61B 5/150221 604/21 |
| 2005/0090820 | A1 | 4/2005 | Cornelius et al. |
| 2005/0261632 | A1 | 11/2005 | Xu |
| 2011/0213335 | A1 | 9/2011 | Burton et al. |
| 2018/0221083 | A1* | 8/2018 | Manstein .............. A61M 5/158 |
| 2020/0360072 | A1* | 11/2020 | Kuang .................. A61B 18/10 |

FOREIGN PATENT DOCUMENTS

| | | | |
|---|---|---|---|
| JP | 2007531578 | A | 11/2007 |
| JP | 2015500090 | A | 1/2015 |
| KR | 20130009512 | A | 1/2013 |
| WO | 9748442 | A1 | 12/1997 |
| WO | 2015052705 | A1 | 4/2015 |

OTHER PUBLICATIONS

China National Intellectual Property Administration, First Office Action and Search Report issued in Chinese Patent Application Serial No. 201980080092.X on Oct. 20, 2023; 9 pages.
Taiwan Intellectual Property Office, First Office Action issued in Patent Application Serial No. 108144516 on Apr. 10, 2023; 14 pages.
The International Bureau of WIPO, International Preliminary Report on Patentability issued Jun. 8, 2021 in International Application No. PCT/EP2019/083850.
European Patent Office, International Search Report and Written Opinion issued Jun. 3, 2020 in PCT/EP2019/083850.
China National Intellectual Property Administration, Second Office Action and Search Report issued in Chinese Patent Application Serial No. 201980080092.X on Apr. 30, 2024; 31 pages.
Australian Intellectual Property Office, Examination Report No. 1 issued in Australian Patent Application No. 2019394080 on Jun. 25, 2024; 4 pages.
Australian Intellectual Property Office, Examination Report No. 2 issued in Australian Patent Application No. 2019394080 on Jul. 18, 2024; 3 pages.
European Patent Office, Communication pursuant to Article 94(3) EPC, Examination Report issued in European Patent Application No. 19817639.8 on Jul. 10, 2024; 4 pages.
Korean Intellectual Property Office, Notice of Preliminary Rejection issued in Korean Patent Application No. 10-2021-7016912 on Oct. 11, 2024; 14 pages.

* cited by examiner

MICROBLADE STRUCTURE AND METHOD OF TREATING TISSUE

FIELD OF THE INVENTION

The invention described herein generally relates to structures for treating tissue with high-frequency energy, methods of making a structure for treating tissue with high-frequency energy, and methods of treating tissue with high-frequency energy.

BACKGROUND

Electromagnetic radiation applied to tissue, e.g. various layers of skin, can have a physiological effect on the tissue's appearance. In particular, treatment with electromagnetic energy can arrest the formation of wrinkles and impart a more youthful skin appearance. High-frequency treatment devices, such as radio-frequency (RF)-based treatment devices, may be used to treat tissue, such as the skin. In some systems, the high-frequency energy may be transmitted transcutaneously from a planar electrode to the tissue. In a microneedling system, an array of electrode needles is used to percutaneously treat the tissue with electromagnetic energy.

High-frequency treatment devices operate by transmitting high-frequency energy to the underlying tissue. The high-frequency energy heats the tissue to a therapeutic temperature sufficient to create micro-injuries in the tissue. The damage from the micro-injuries stimulates a healing response that causes collagen fibers in the tissue to shrink and contract. The healing response may also stimulate collagen production that can result in additional tissue contraction. The tissue contraction may result in tissue tightening. For applications in treating skin tissue, the tissue contraction may reduce wrinkles and skin laxity, and may lessen acne scarring.

Conventional microneedling systems employ needles that perform the dual functions of penetrating into the tissue and transferring high-frequency energy to the tissue in which the needles are inserted. The needle arrays may be constructed from round needles that taper with a conical shape to a sharp point, and that are arranged in a rectangular array. Conventional needle arrays used in microneedling systems may be difficult to manufacture, may cause significant pain to the patient when being inserted into the tissue, and can easily become unusable after repeated insertion due to dulling.

Therefore, a need exists for improved structures for treating tissue with high-frequency energy, methods of making a structure for treating tissue with high-frequency energy, and methods of treating tissue with high-frequency energy.

SUMMARY

In an embodiment, a structure includes a plurality of microblades composed of an electrical conductor. The microblades each include a shaft and a tip adjacent to an end of the shaft. The tip includes a plurality of surfaces that taper toward the end of the shaft. The plurality of surfaces are arranged to surround a solid core of the tip.

In another embodiment, a method includes applying an etch mask to a plate and etching first portions of the plate that are unmasked by the etch mask with an etching process to completely remove the first portions of the plate. The plate includes second portions that are masked by the etch mask during the etching process, the second portions include a plurality of microblades each having a shaft and a tip adjacent to an end of the shaft, and the tip includes a plurality of surfaces that taper toward the end of the shaft.

In another embodiment, a treatment method includes inserting a plurality of microblades arranged in a rhombus-shaped pattern to a given depth into tissue, energizing the plurality of microblades in alternating rows of the rhombus-shaped pattern with opposite polarities of radio-frequency energy, and treating the tissue with the radio-frequency energy.

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the invention. In the drawings, like reference numerals are used to indicate like features in the various views.

DETAILED DESCRIPTION

Figure 1:
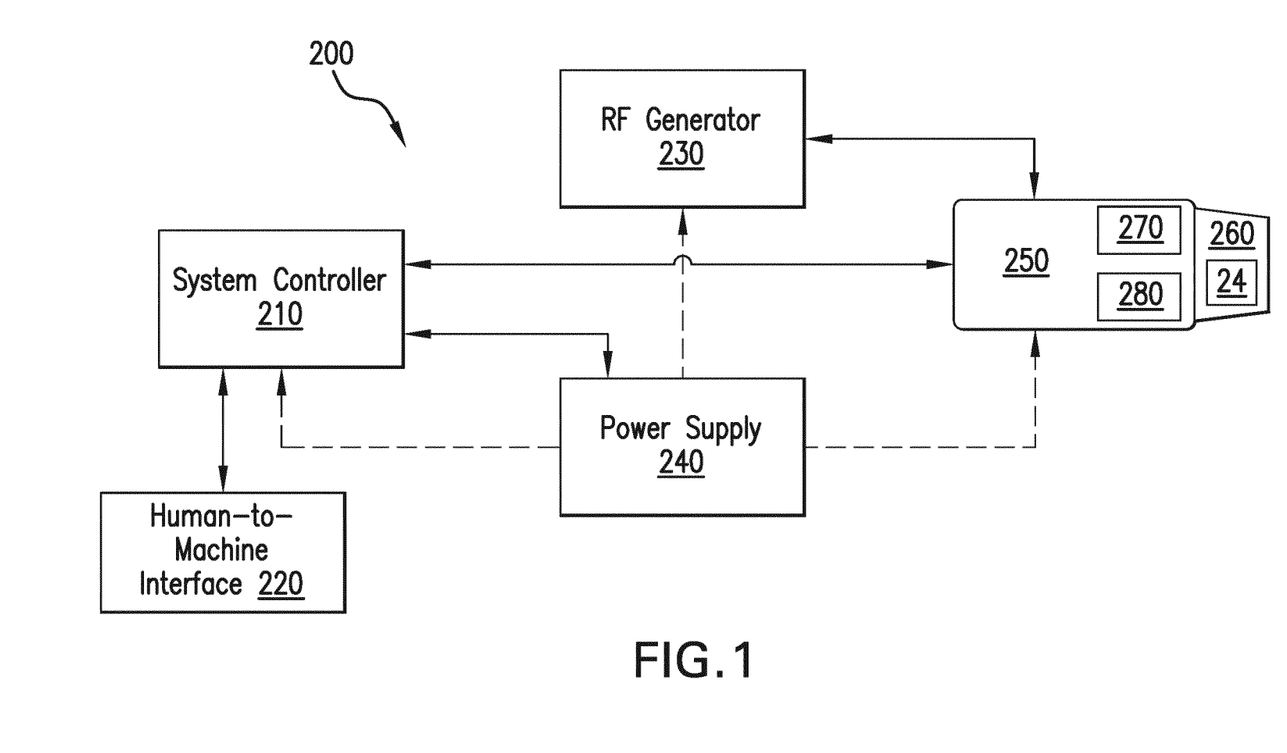
FIG. 1 is a block diagram of an example energy-based therapeutic device that is suitable for implementing aspects of the embodiments of the invention described herein.

With reference to FIG. 1 and in accordance with embodiments of the invention, an energy-based therapeutic device 200 includes a system controller 210, a human-to-machine interface ("HMT") 220, a high-frequency generator 230, a power supply 240, a handpiece 250, and a treatment tip 260. The system controller 210 is generally configured to control the operation and functionality of the device 200 by controlling the other components of the device 200, such as the high-frequency generator 230 and the power supply 240. The system controller 210 is a high-level hardware controller that enables the application of high-frequency energy (e.g., radio-frequency (RF) energy) to a treatment area of a patient for use in, for example, a transcutaneous dermatological treatment. Lower level hardware controllers located in the other components of the device 200 may manage component-level operations under the direction and coordination of the system controller 210.

In controlling and orchestrating the operation of the other components, the system controller 210 may also monitor status messages received from the lower-level hardware controllers and various operational parameters during a procedure applying high-frequency energy to the treatment area. Examples of such operational parameters include: the peak/average output power emitted from the treatment tip 260, the temperature at the treatment tip 260, the patient-applied mechanical force, current values of usage data for the treatment tip, and the like. The system controller 210 may disable the application of high-frequency energy to the treatment area if the operational parameters or the status messages from the lower-level hardware controllers indicate a fault condition. For example, if a current value of usage data for the treatment tip 260 exceeds a threshold value, the system controller 210 will disable the application of high-frequency energy to the treatment area.

The HMI 220 provides an interface between an operator (e.g., a clinician) and the device 200 for exchanging commands, requests, information, data, and the like, which enable the operator to interact with the functionalities provided by the device 200. In an embodiment, the HMI 220 may include a touch-sensitive touch screen that provides both an input interface and an output interface between the operator and the device 200. In an embodiment, the HMI 220 may include an audio interface, such as a microphone and/or speaker. In an embodiment, the HMI 220 may include physical input devices, such as buttons (e.g., push buttons, rocker buttons, etc.), dials, slider switches, joysticks, click wheels, a keyboard, a pointer device (e.g., a mouse), and the like. The high-frequency generator 230 is configured to generate high-frequency (e.g., RF energy) for driving the film electrodes 51 in the treatment tip 260 when enabled by the system controller 210 and in accordance with commands received from an operator via the HMI 220. In an embodiment, the high-frequency energy may be radio-frequency energy in a range from one (1) megahertz (MHz) to twenty (20) megahertz.

The power supply 240 is configured to deliver electrical power from an external power source (e.g., an alternating current ("AC") outlet) to the various components of the device 200. In an embodiment, the power supply 240 is configured to convert AC power obtained from an external power source into direct current ("DC") power for delivery to the various components. In an embodiment, the power supply 240 may be configured to provide electrical isolation between the external power source and the other components of the device 200.

The handpiece 250 is configured to couple the treatment tip 260 to the other components of the device 200 along the high-frequency energy propagation path. The handpiece 250 may be connected to the device 200 via a flexible conduit enclosing conductors that electrically couple the handpiece 250 to the other components. The handpiece 250 may have a smoothly contoured grip for gripping and handling by a clinician serving as the operator, which permits the handpiece 250 to be grasped by at least one hand of the clinician for manipulating the location of the handpiece 250 and the treatment tip 260. During a therapeutic procedure, an operator positions the handpiece 250 (and thereby the treatment tip 260 and its assembly 24) proximate to a treatment area of a patient and in contact with the treatment area After inserting the microblades into the treatment area, as subsequently described, the operator may instruct the device 200 to deliver high-frequency energy from the assembly 24 to the treatment area by interacting with controls disposed on an outward surface of the handpiece 250 and/or controls at the console. For example, the handpiece 250 may include controls that enable the operator to initiate/terminate high-frequency energy delivery to the treatment area and/or adjust an amount of high-frequency energy that is applied to the treatment area.

The treatment tip 260 couples with the handpiece 250 to deliver high-frequency energy generated by high-frequency generator 230 to a patient for therapeutic purposes. The treatment tip 260 may include microblades 12 (FIGS. 2, 2A, and 3) that are designed to deliver the high-frequency energy in a specific pattern and density to the patient during the therapeutic procedure. The treatment tip 260 may include a housing in which the assembly 24, which includes the microblades 12, is contained and may be configured so as to be releasably attached to the handpiece 250. Sensor data indicative of a temperature at the treatment tip 260 may be obtained using temperature sensors (e.g., thermistors) that are included in the treatment tip 260.

In an embodiment, at least a subset of the components forming the device 200 are contained within a console (or mechanical enclosure). For example, the console may contain the system controller 210, the high-frequency generator 230, and the power supply 240. In an embodiment, the handpiece 250 is physically coupled to the console via the flexible conduit enclosing conductors that electrically couple the handpiece 250 to the other components of the device 200. All or part of the HMI 220 may be disposed on an outward facing surface of the console.

A fluid delivery member 270 may be arranged inside the handpiece 250 and/or the treatment tip 260. A supply of coolant (e.g., a coolant canister) may be located at the console of the device 200 and coupled by tubing with the fluid delivery member 270. The fluid delivery member 270 may be configured to controllably deliver a spray or stream of a coolant to the assembly 24 in conjunction with a treatment procedure. The coolant may be triggered under the control of the system controller 210 to deliver the coolant spray or stream before, during, and/or after the delivery of the high-frequency energy from the assembly 24 to the patient's tissue.

A vibration device 280 may be arranged inside the handpiece 250 and/or the treatment tip 260. The vibration device 280 is configured to oscillate or vibrate the treatment tip 260 and assembly 24 at a relatively low frequency relative to the handpiece 250 and the treatment area. In particular, the vibration device 260 causes the treatment tip 260 to oscillate or vibrate in a linear path along an axis that is normal or substantially normal to the treatment area with at least a portion of the treatment tip 260 in contact with the treatment area to transfer the vibration to the treatment area. Without intending to be bound by any particular theory, it is believed that such vibration may provide a pain control mechanism for the patient during a treatment procedure and may also ease insertion of the microblades 12 into the tissue.

Figure 2:
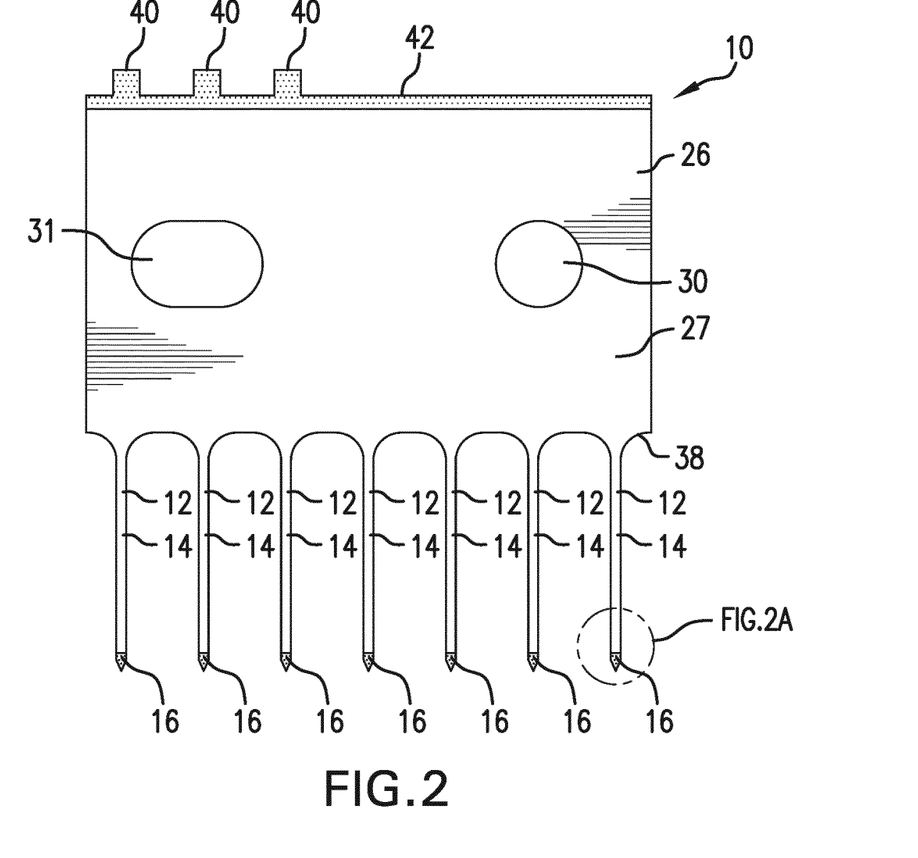
FIG. 2 is a front view of a structure in accordance with embodiments of the invention.
Figure 2A:
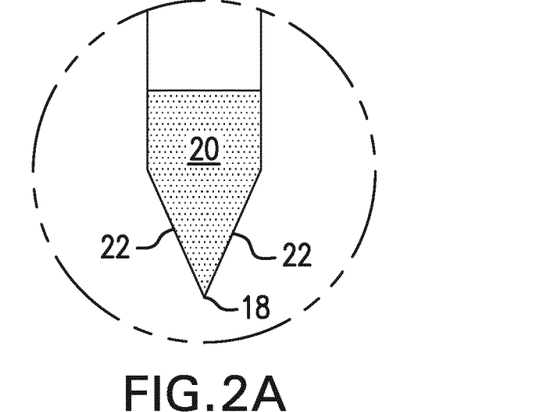
FIG. 2A is an enlarged view of the circled region of FIG. 2.
Figure 3:
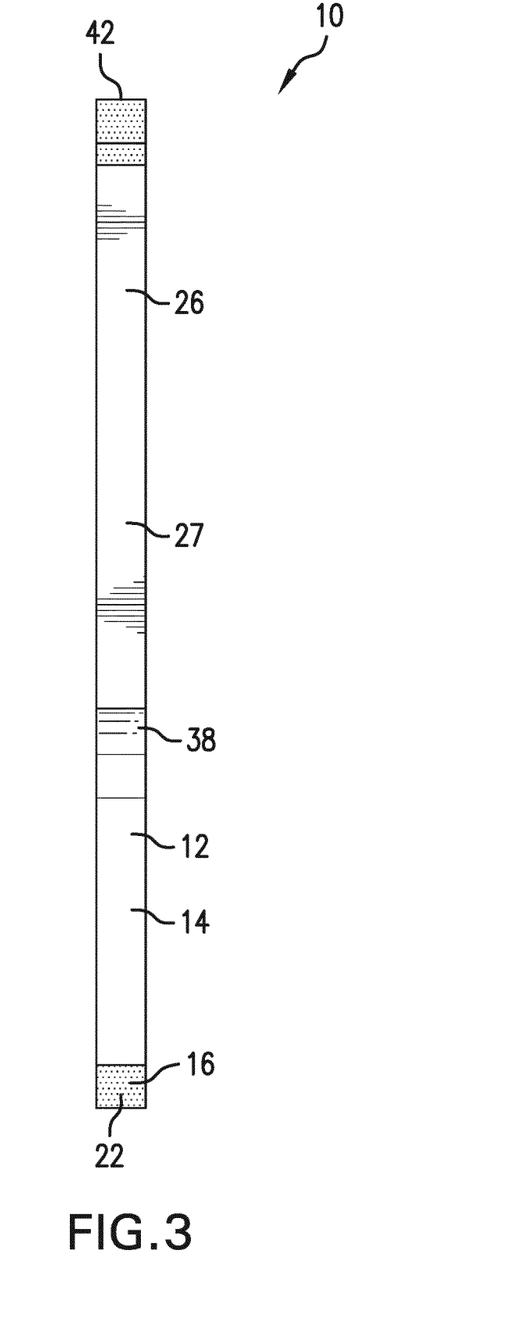
FIG. 3 is a side view of the structure of FIG. 2.

With reference to FIGS. 2, 2A, and 3 and in accordance with embodiments of the invention, a microblade panel 10 includes a plate 26 and multiple microblades 12 that project from the plate 26. Each of the microblades 12 has a shaft 14 connected at one end to a side edge 38 of the plate 26 and a tip 16 that is arranged at an opposite end of the shaft 14.

All or a portion of the tip 16 of each microblade 12 is shaped to penetrate into tissue during a treatment procedure. The microblades 12 may be arranged with a given pitch that provides a uniform spacing between the tips 16.

As best shown in FIGS. 2, 3, the shaft 14 of each microblade 12 may include surfaces 20, 22 that are arranged to alternate with each other around the periphery of the shaft 14 such that one of the surfaces 20 is arranged between a pair of the surfaces 22. In an embodiment, each of the surfaces 20, 22 may be flat and planar, and may lack any curvature. The surfaces 20 are separated by a thickness of the shaft 14, which may be equal or substantially equal to the thickness of the plate 26. The surfaces 22, which connect the surfaces 20, are arranged to extend across the thickness of the plate 26. The entire shaft 14, including the tip 16, may be solid with the surfaces 20, 22 being arranged to surround a solid core composed of a conductor.

The surfaces 22 taper at the tip 16 and converge to define an edge 18 that terminates the shaft 14. The edge 18 is capable of puncturing or piercing a tissue surface in a manner analogous to a blade and then penetrating to a shallow depth into the underlying tissue during a treatment procedure. In that regard, the edge 18 may have a linear shape similar to a blade, which differs from the shape of conventional round needles that have conical tips converging to a point. The shape of the tip 16 and edge 18 may improve the sharpness and longevity of the microblades 12 in comparison with conventional round needles having conical tips.

The plate 26 has a side edge 42 that is opposite to the side edge 38, and one or more tabs 40 are arranged at the side edge 42. The tabs 40 are used to establish electrical connections with the microblade panel 10 and its microblades 12, as described below. The tabs 40 project from the side edge 42 to provide clearance that assists in establishing the electrical connections.

Alignment openings 30, 31 are arranged between the side edges 38, 42 of the plate 26 and extend fully through the thickness of the plate 26. The alignment openings 30, 31, which are used to assemble multiple microblade panels into an assembly, may have different geometrical shapes. For instance, the alignment opening 30 may have a circular shape, and the alignment opening 31 may have an oval shape. As described below, the alignment openings 30, 31 are used to form an assembly including multiple microblade panels 10. In an alternative embodiment, not shown, a single alignment opening (e.g., alignment opening 30) may be present.

The microblades 12 and the plate 26 of the microblade panel 10 may have an integral construction, instead of being constructed as an assembly as in conventional microneedling systems. The integral construction originates from the manner in which the microblade panel 10 is formed. The microblades 12 and plate 26 may be composed of any suitable conductor, such as stainless steel, copper, nitinol, silver, aluminum, graphite, or a combination of these metals. The microblade panel 10 may be formed by applying an etch mask to a sheet of the conductor and fully removing portions of the sheet that are unmasked by the etch mask with an etching process. The microblades 12 and plate 26 represent portions that are masked and protected by the etch mask during the etching process.

A dielectric coating 27 may be formed on each shaft 14 at a location arranged between the tip 16 and the side edge 38 of the plate 26. The tip 16, which is inserted into the tissue during treatment, is not covered by the dielectric coating 27 and may directly contact the tissue. The plate 26 is also partially coated by the dielectric coating 27 with at least the tabs 40 along the side edge 42 being uncoated to promote the formation of an electrical connection with the plate 26. The dielectric coating 27 may be composed of any suitable dielectric material, such as parylene or silicon dioxide, that is an electrical insulator. The dielectric coating 27 may be applied by dipping, physical vapor deposition, sputter deposition, or a combination of two or more of these methods. In an embodiment, the dielectric coating 27 may be composed of parylene deposited by physical vapor deposition. In an embodiment, the dielectric coating 27 may be composed of silicon dioxide deposited by sputter deposition. In an embodiment, a mechanical masking process may be used to prevent the dielectric coating 27 from being applied to the tabs 40 and the tips 16. After the mechanical mask is applied, the exposed surfaces may be coated with the dielectric coating 27. Then the mechanical mask may be removed, leaving the tabs 40 and the tips 16 uncoated with the dielectric coating 27 and the remainder of shafts 14 and plate 26 coated with the dielectric coating 27.

Figure 4A:
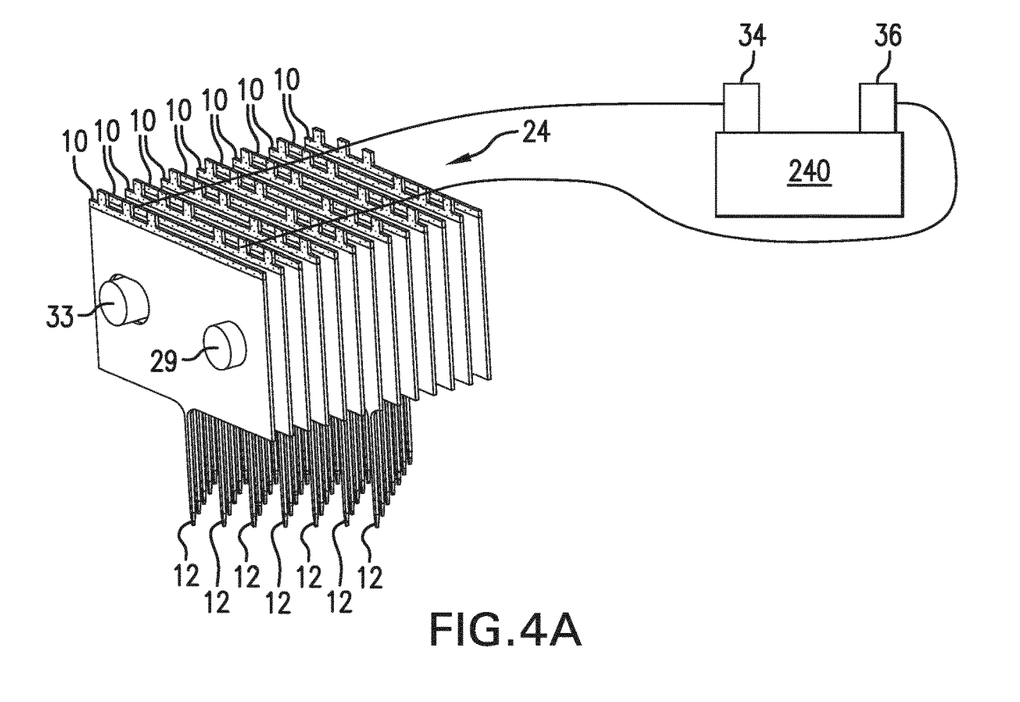
FIG. 4A is a perspective view of an assembly in accordance with embodiments of the invention.
Figure 4B:
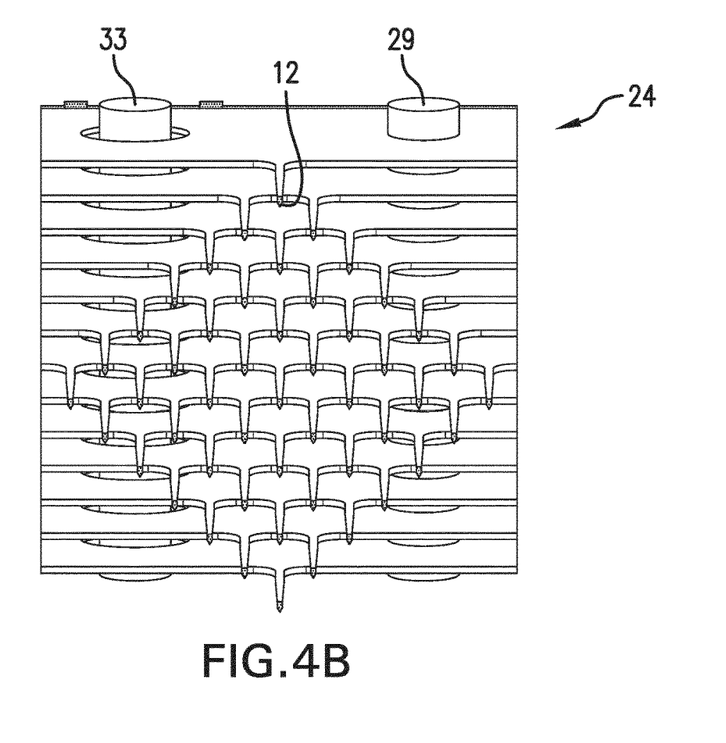
FIG. 4B is a bottom view of the assembly of FIG. 4A.
Figure 5A:
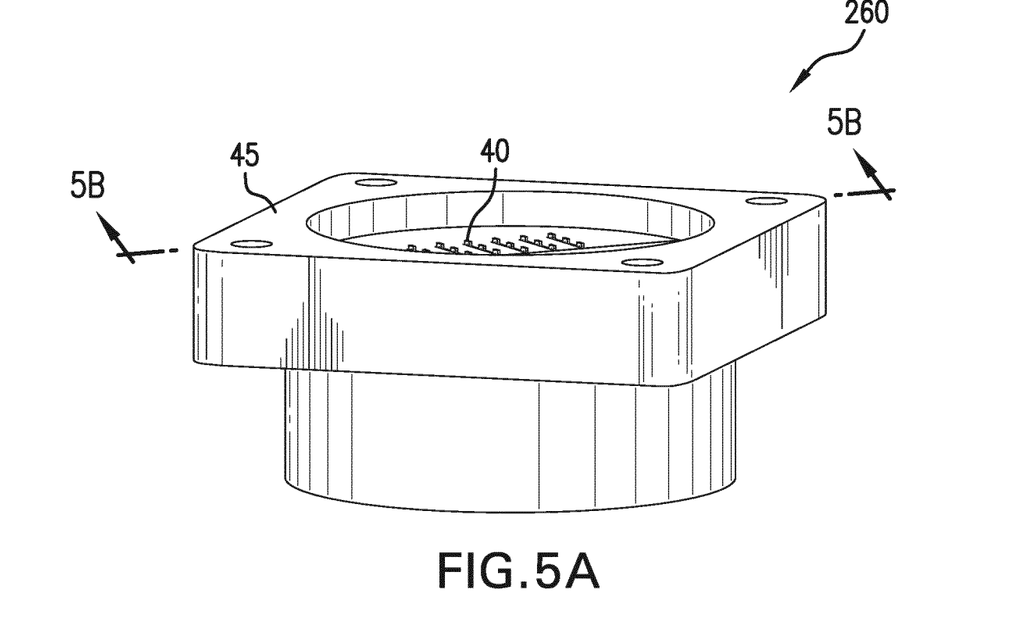
FIG. 5A is a perspective view of a treatment tip in accordance with embodiments of the invention.
Figure 5B:
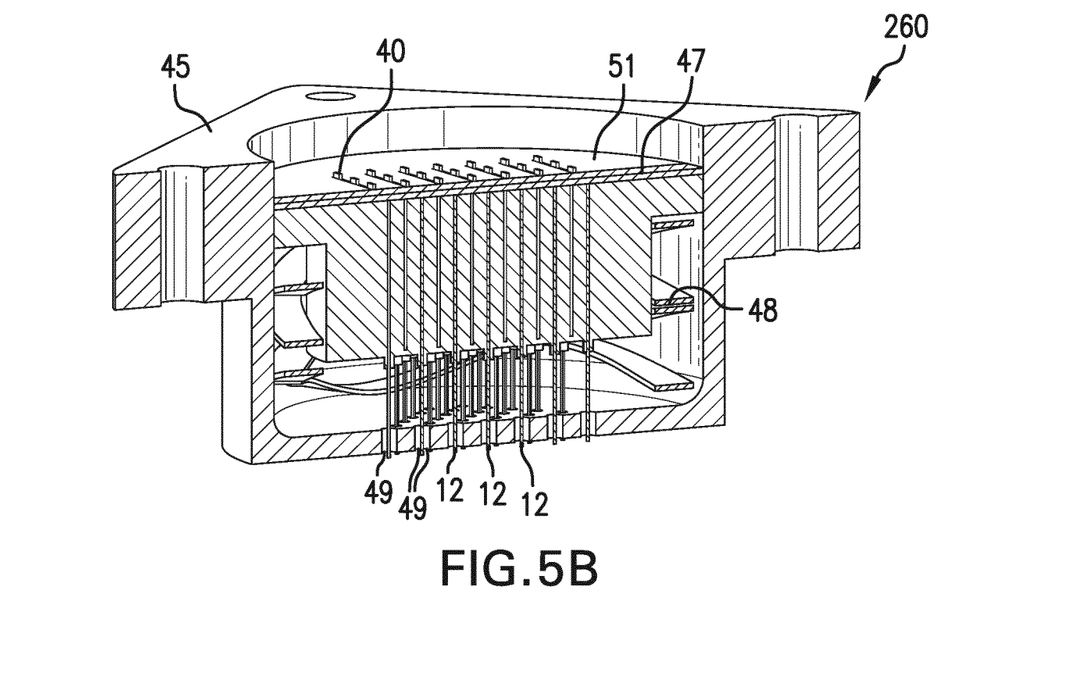
FIG. 5B is a cross-sectional view of the treatment tip of FIG. 5A.

With reference to FIGS. 4A and 4B and in accordance with embodiments of the invention, an assembly 24 includes multiple microblade panels 10 that are assembled together in a stacked arrangement. Each of the microblade panels 10 in the assembly 24 may include at least one of the microblades 12. In some embodiments, adjacent pairs of the microblade panels 10 in the assembly 24 may include different numbers of microblades 12. For instance, the different numbers in the adjacent pairs of microblade panels 10 may increase (i.e., increment) or decrease (i.e., decrement) by unity. The microblade panels 10 in the assembly 24 may thus be arranged to place the tips 16 of the microblades 12 in a diamond-shaped (or rhombus-shaped) array. The dielectric coating 27 on the plates 26 may electrically isolate or assist in electrically isolating the individual plates 26 in the assembly 24 from each other.

Alignment rods 29, 33 may be inserted through the alignment openings 30, 31 of the microblade panels 10 for purposes of aligning the microblade panels 10 relative to each other in the assembly 24 and to position the tips 16 of the microblades 12 in the diamond-shaped array of the assembly 24. The alignment rod 29 in the alignment openings 30 may be used to orient the microblade panels 10 relative to each other, and the alignment rod 33 in the alignment openings 31 may be used to locate the microblade panels 10 relative to each other. In an embodiment with a single alignment opening, not shown, the single alignment opening can be used to both orient and locate the microblade panels 10 relative to each other.

The microblade panels 10 in the assembly 24 may be connected with an output terminal 34 and an output terminal 36 of the power supply 240 such that the plates 26 have alternating connections to the different terminals 34, 36. The output terminal 34 of the power supply 240 may be a bipolar power supply that outputs a positive polarity of high-frequency alternating current, and the output terminal 36 of the bipolar power supply 240 may output a negative polarity of the high-frequency alternating current. In some embodiments, the power supply 240 may operate at a frequency of about 0.1 to about 0.2 MHz, or about 0.2 to about 0.3 MHz, or about 0.3 to about 0.4 MHz, or about 0.4 to about 0.5 MHz, or about 0.5 to about 0.6 MHz, or about 0.6 to about 0.7 MHz, or about 0.7 to about 0.8 MHz, or about 0.8 to about 0.9 MHz, or about 0.9 to about 1 MHz, or about 1 to about 2 MHz, or about 2 to about 3 MHz, or about 3 to about 4 MHz, or about 4 to about 5 MHz, or about 5 to about 6 MHz, or about 6 to about 7 MHz, or about 7 to about 8 MHz, or about 8 to about 9 MHz, or about 9 to about 10 MHz, or about 10 to about 11 MHz, or about 11 to about 12 MHz, or about 12 to about 13 MHz, or about 13 to about 14 MHz, or about 14 to about 15 MHz, or about 15 to about 16 MHz, or about 16 to about 17 MHz, or about 17 to about 18 MHz, or about 18 to about 19 MHz, or about 19 to about 20 MHz. In some embodiments, the power supply 240 may operate at a frequency of about 6.78 MHz or about 13.56 MHz. In some embodiments, the power supply 240 may operate with a frequency range of 0.1 to 10 MHz or from a narrower frequency range of 0.4 to 3 MHz.

The tabs 40 of one of the plates 26 in each of the adjacent pairs of the microblade panels 10 in the assembly 24 may be connected to the output terminal 34, and the tabs 40 of the other of the plates 26 in each of the adjacent pairs of the microblade panels 10 in the assembly may be connected to the output terminal 36 of opposite polarity. To that end, the tabs 40 of the plates 26 may be systematically and alternatingly arranged in the assembly 24 to permit the alternating electrical connections to be made with either the output terminal 34 or the output terminal 36 of the power supply 240. For example, the tabs 40 on each adjacent pair of the plates 26 may be placed on the side edge 42 to permit one of the plates 26 in each adjacent pair to be connected with the output terminal 34 of the power supply 240 and to permit the other of the plates 26 in each adjacent pair to be connected with the output terminal 36 of the power supply 240.

Figure 6A:
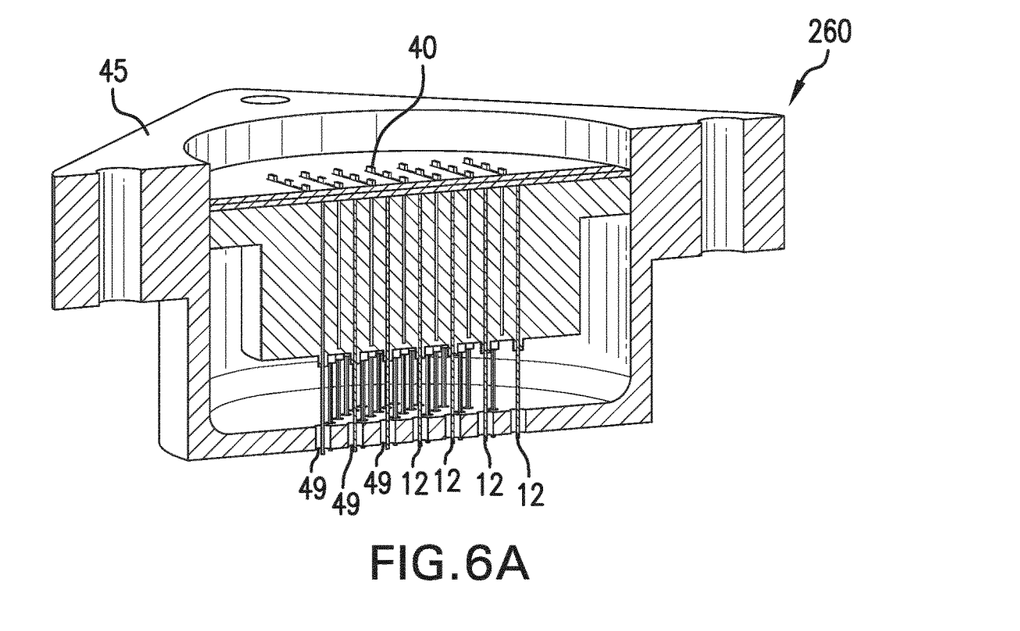
FIG. 6A is a cross-sectional diagrammatic view of a treatment tip in which the tips of the microblades are retracted inside the treatment tip in accordance with embodiments of the invention.
Figure 6B:
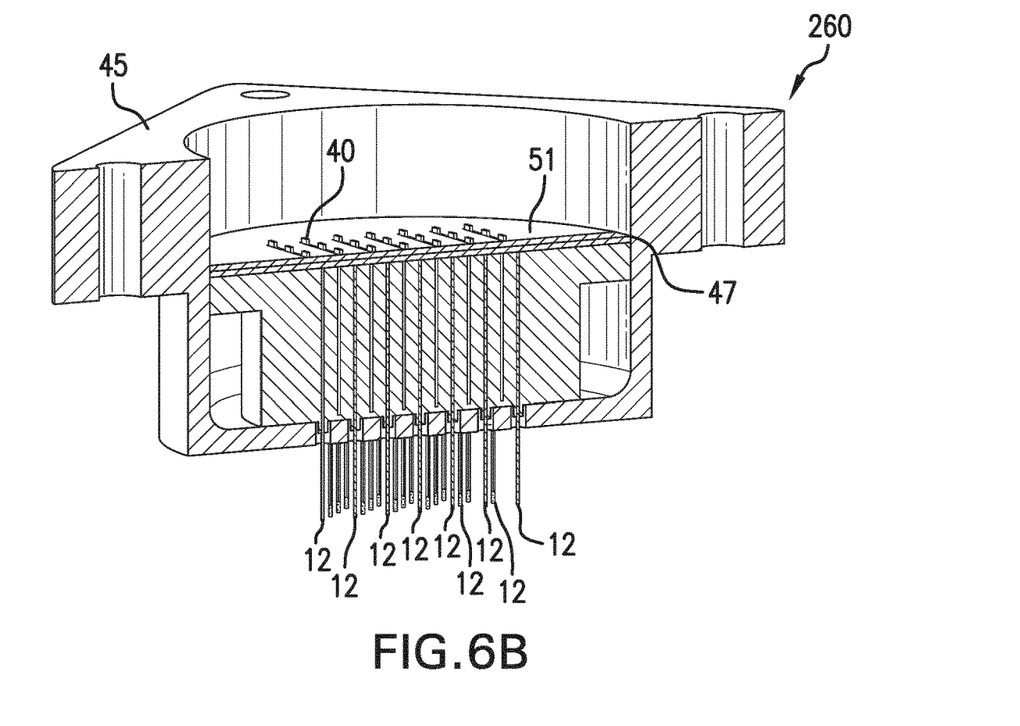
FIG. 6B is a cross-sectional diagrammatic view of a treatment tip in which the tips of the microblades are extended from the treatment tip in accordance with embodiments of the invention.

With reference to FIGS. 5A, 5B, 6A, 6B and in accordance with embodiments of the invention, a treatment tip 260 may include a cartridge or housing 45 that includes openings 49, and the assembly 24 may be placed inside the housing 45 with the microblades 12 generally aligned with the openings 49. The treatment tip 260 may be a disposable item that is releasably attached to the handpiece 250 or, alternatively, may be reusable. The assembly 24 may be spring-loaded relative to the housing 45 of the treatment tip 260 by a spring 48 such that the assembly 24 can move relative to the treatment tip 260 between an extended position in which the tips 16 of the microblades 12 project from the housing 45 of the treatment tip 260, as shown in FIG. 6B, and a retracted position in which the tips 16 of the microblades 12 are retracted into the housing 45 of the treatment tip 260, as shown in FIG. 6A. Specifically, the spring 48 may be arranged between the housing 45 and a flange 47 connected with the assembly 24 to provide the spring-loading.

The microblades 12 are initially arranged within the treatment tip 260 such that the tips 16 are retracted and hidden inside the housing 45. When the practitioner places the treatment tip 260 in contact with the tissue surface, a force applied through the handpiece 250 and treatment tip 260 to the assembly 24 that is greater than the opposing spring force of the spring 48 causes the assembly 24 to move within the housing 45 such that the microblades 12 move outwardly through the openings 49 and the tips 16 contact the tissue surface and pierce the tissue. The practitioner can then cause the high-frequency energy to be applied through the tips 16 to treat a region of the tissue. For example, the tips 16 may penetrate through the epidermis and into the dermis of skin tissue and produce micro-injuries in the dermis in response to the application of high-frequency energy without damaging the epidermis. The tips 16, due to their non-circular shape, may provide a larger surface area than the conical tip of a conventional round needle, which may improve electrical conduction to the dermis in comparison with a conventional round needle. When the handpiece 250 is lifted away from the tissue after treating a region, either to complete the procedure or to move the treatment device to another region, the force applied by the handpiece 250 and treatment tip 260 to the assembly 24 is removed and the spring 48 is freed to expand, which causes the microblades 12 to move within the openings 49 in the housing 45 and, in particular, the tips 16 to retract back into the treatment tip 260.

The tabs 40 on the plates 26 in the assembly 24 are connected to film electrodes 51 that are located over the flange 47. As depicted, the tabs 40 of every other plate 26 are all connected with one of the film electrodes 51. The tabs 40 of the intervening plates 26, which are not visible in FIGS. 5A, 5B, 6A, 6B, are all connected with the other of the film electrodes 51.

Figure 7:
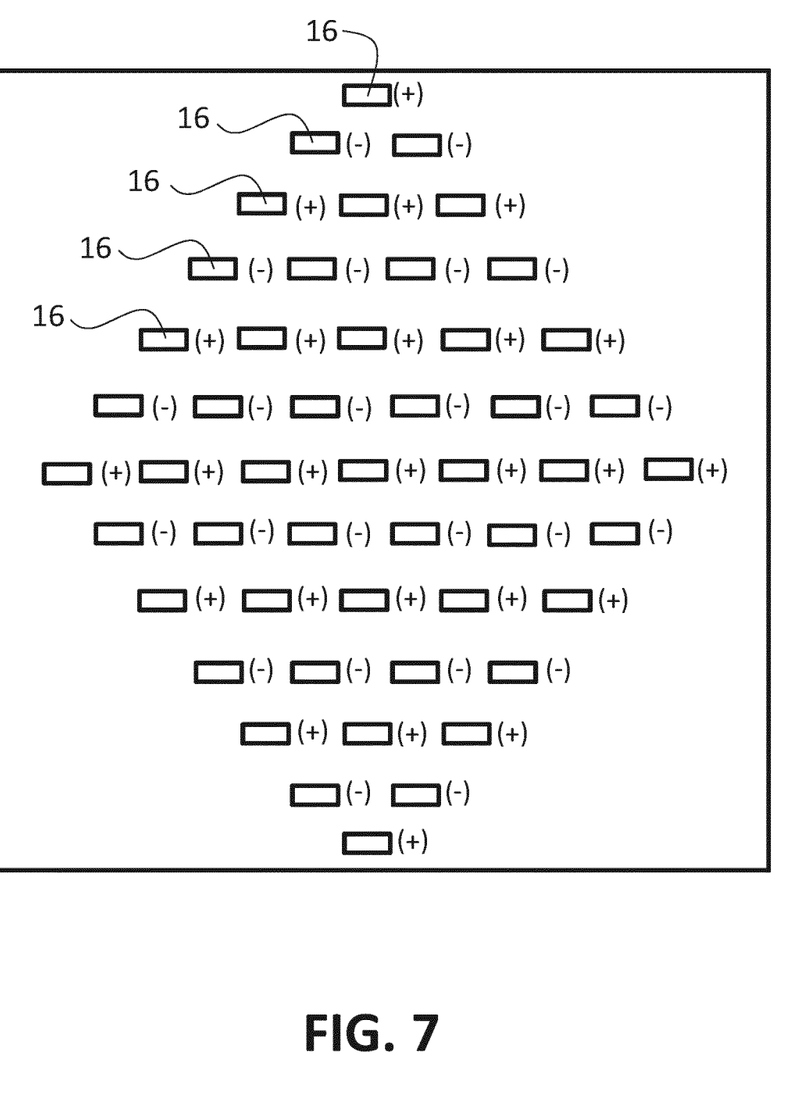
FIG. 7 is a diagrammatic bottom view of the tips of the microblades of an assembly in accordance with embodiments of the invention.

During a treatment procedure, the tips 16 of the microblades 12 in the assembly 24 are arranged in a diamond-shape (or rhombus-shaped) pattern and penetrate to a given depth into tissue. The microblades 12 and tips 16 in alternating rows of the diamond-shaped pattern are energized with opposite polarities of the high-frequency (e.g., radio-frequency (RF)) energy, as best shown in FIG. 7, and the tissue is treated with the high-frequency energy. As shown in FIG. 7, the microblade panels 10 with different numbers of microblades 12 in the assembly 24 have tips 16 that are powered with alternating polarities—either positive (+) or negative (−). Such a rhombus-shaped pattern may be contrasted with a conventional square-shaped or rectangular-shaped array of needles, which produce different heating patterns than those produced by the rhombus-shaped patterns of embodiments described herein. For instance, heating patterns produced by rectangular-shaped arrays may be less uniform than those produced by the rhombus-shaped patterns of embodiments described herein.

In general, the portions of the tissue in which the tips 16 are embedded experience a temperature rise in response to the application of the high-frequency energy. The temperature rise creates micro-injuries in a portion of the tissue locally surrounding each of the embedded tips 16. Following treatment, the damage from the micro-injuries may stimulate a healing response that causes collagen fibers in the tissue to shrink and contract, and that may also stimulate collagen production that can result in additional tissue contraction. The tissue contraction may result in tissue tightening for treating conditions of skin tissue such as wrinkles, skin laxity, and acne scarring.

References herein to terms such as "vertical," "horizontal," etc. are made by way of example, and not by way of limitation, to establish a frame of reference. It is understood that various other frames of reference may be employed for describing the invention without departing from the spirit and scope of the invention. It is also understood that features of the invention are not necessarily shown to scale in the drawings. Furthermore, to the extent that the terms "composed of," "includes," "having," "has," "with," or variants thereof are used in either the detailed description or the claims, such terms are intended to be inclusive and open-ended in a manner similar to the term "comprising."

References herein to terms modified by language of approximation, such as "about", "approximately", and "substantially", are not to be limited to the precise value specified. The language of approximation may correspond to the precision of an instrument used to measure the value and, unless otherwise dependent on the precision of the instrument, may indicate +1-10% of the stated value(s).

A feature "connected" or "coupled" to or with another feature may be directly connected or coupled to or with the other feature or, instead, one or more intervening features may be present. A feature may be "directly connected" or "directly coupled" to or with another feature if intervening features are absent. A feature may be "indirectly connected" or "indirectly coupled" to or with another feature if at least one intervening feature is present. A feature "on" or "contacting" another feature may be directly on or in direct contact with the other feature or, instead, one or more intervening features may be present. A feature may be "directly on" or in "direct contact" with another feature if intervening features are absent. A feature may be "indirectly on" or in "indirect contact" with another feature if at least one intervening feature is present.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of applicants' general inventive concept.

What is claimed is:

1. A structure for applying high-frequency energy, the structure comprising:
   a plurality of microblades comprising an electrical conductor, each of the plurality of microblades including a shaft and a tip adjacent to an end of the shaft, the shaft including a first portion, the tip including a plurality of surfaces arranged to surround a solid core of the tip, and at least two of the plurality of surfaces tapering toward the end of the shaft;
   a plurality of plates comprising the electrical conductor and having a stacked arrangement, each of the plurality of plates including at least one of the plurality of microblades and a plurality of surfaces, and the first portion of the shaft of each of the plurality of microblades attached to one of the plurality of plates; and
   a dielectric coating arranged on the plurality of surfaces of each of the plurality of plates.

2. The structure of claim 1 wherein each of the plurality of surfaces of the tip of each of the plurality of microblades is planar.

3. The structure of claim 1 wherein the shaft further includes a second portion, the tip is arranged on the second portion of the shaft, and the dielectric coating is further arranged on the second portion of the shaft of each of the plurality of microblades.

4. The structure of claim 1 wherein the stacked arrangement of the plurality of plates places the plurality of microblades in a rhombus-shaped array.

5. The structure of claim 1 wherein each of the plurality of plates includes at least one alignment opening.

6. The structure of claim 1 wherein each of the plurality of plates includes a first alignment opening and a second alignment opening spaced from the first alignment opening, the first alignment opening having a circular shape and the second alignment opening having an oval shape.

7. The structure of claim 1 wherein the plurality of surfaces of each of the plurality of microblades include a first planar surface, a second planar surface separated from the first planar surface by a thickness of the shaft, and a pair of inclined surfaces that connect opposite edges of the first planar surface and the second planar surface.

8. The structure of claim 1 wherein adjacent pairs of the plurality of plates in the stacked arrangement include different numbers of the plurality of microblades.

9. The structure of claim 8 wherein the different numbers in the adjacent pairs increment or decrement by unity.

10. The structure of claim 1 further comprising:
    a treatment tip,
    wherein the plurality of plates are arranged as an assembly inside the treatment tip.

11. The structure of claim 10 wherein the assembly is spring-loaded for movement between a first position in which the tip of each the plurality of microblades is extended from the treatment tip and a second position in which the tip of each of the plurality of microblades is retracted into the treatment tip.

12. The structure of claim 1 further comprising:
    a power supply having a first output terminal and a second output terminal,
    wherein the plurality of plates are arranged in adjacent pairs in the stacked arrangement, and one of the plurality of plates in each of the adjacent pairs is connected to the first output terminal and the other of the plurality of plates in each of the adjacent pairs is connected to the second output terminal.

13. The structure of claim 12 wherein the at least one of the plurality of microblades extends from a first side edge of each of the plurality of plates, each of the plurality of plates includes one or more tabs arranged at a second side edge of each of the plurality of plates that is opposite to the first side edge, and the one or more tabs of each of the plurality of plates are configured to establish an electrical connection with either the first output terminal or the second output terminal of the power supply.

14. The structure of claim 13 wherein the one or more tabs on each adjacent pair of the plurality of plates are placed on the second side edge to permit the electrical connection of one of the plurality of plates in each adjacent pair to the first output terminal of the power supply and to permit the electrical connection of the other of the plurality of plates in each adjacent pair to the second output terminal of the power supply.

15. A structure for applying high-frequency energy, the structure comprising:
    a plurality of microblades comprising an electrical conductor, each of the plurality of microblades including a shaft and a tip adjacent to an end of the shaft, the tip including a plurality of surfaces arranged to surround a solid core of the tip, and at least two of the plurality of surfaces tapering toward the end of the shaft;
    a plurality of plates having a stacked arrangement, each of the plurality of plates including at least one of the plurality of microblades; and
    a power supply having a first output terminal and a second output terminal,
    wherein the plurality of plates are arranged in adjacent pairs in the stacked arrangement, and one of the plurality of plates in each of the adjacent pairs is connected to the first output terminal and the other of the plurality of plates in each of the adjacent pairs is connected to the second output terminal.

16. The structure of claim 15 wherein the adjacent pairs of the plurality of plates in the stacked arrangement include different numbers of the plurality of microblades.

17. The structure of claim 15 wherein the plurality of surfaces of each of the plurality of microblades include a first planar surface, a second planar surface separated from the first planar surface by a thickness of the shaft, and a pair of inclined surfaces that connect opposite edges of the first planar surface and the second planar surface.

18. The structure of claim 15 wherein the at least one of the plurality of microblades extends from a first side edge of each of the plurality of plates, each of the plurality of plates includes one or more tabs arranged at a second side edge of each of the plurality of plates that is opposite to the first side edge, and the one or more tabs of each of the plurality of plates are configured to establish an electrical connection with either the first output terminal or the second output terminal of the power supply.

19. The structure of claim 18 wherein the one or more tabs on each adjacent pair of the plurality of plates are placed on the second side edge to permit the electrical connection of one of the plurality of plates in each adjacent pair to the first output terminal of the power supply and to permit the electrical connection of the other of the plurality of plates in each adjacent pair to the second output terminal of the power supply.

20. A treatment method comprising:
   inserting respective tips of a plurality of microblades arranged in a rhombus-shaped pattern to a given depth into tissue;
   energizing the plurality of microblades in alternating rows of the rhombus-shaped pattern with opposite polarities of radio-frequency energy; and
   treating the tissue with the radio-frequency energy delivered from the respective tips of the plurality of microblades.

* * * * *